(12) United States Patent
Zhang et al.

(10) Patent No.: US 11,333,585 B2
(45) Date of Patent: May 17, 2022

(54) DEVICE FOR CONTINUOUSLY SAMPLING DEEP SEA SURFACE WATER

(71) Applicant: THE FIRST INSTITUTE OF OCEANOGRAPHY, MNR, Shandong (CN)

(72) Inventors: Zhiping Zhang, Shandong (CN); Haoran Zhang, Shandong (CN); Yang Li, Shandong (CN)

(73) Assignee: THE FIRST INSTITUTE OF OCEANOGRAPHY, Shandong (CN)

( * ) Notice: Subject to any disclaimer, the term of this patent is extended or adjusted under 35 U.S.C. 154(b) by 139 days.

(21) Appl. No.: 16/962,532

(22) PCT Filed: Apr. 2, 2019

(86) PCT No.: PCT/CN2019/081047
§ 371 (c)(1),
(2) Date: Jul. 16, 2020

(87) PCT Pub. No.: WO2019/196711
PCT Pub. Date: Oct. 17, 2019

(65) Prior Publication Data
US 2020/0378873 A1   Dec. 3, 2020

(30) Foreign Application Priority Data
Apr. 13, 2018 (CN) .......................... 201810388674.1

(51) Int. Cl.
*G01N 1/14* (2006.01)
*G01B 21/18* (2006.01)
*G01N 33/18* (2006.01)

(52) U.S. Cl.
CPC ............... *G01N 1/14* (2013.01); *G01B 21/18* (2013.01); *G01N 33/18* (2013.01); *G01N 2001/1418* (2013.01)

(58) Field of Classification Search
CPC .................................. G01N 1/10; G01N 1/14
See application file for complete search history.

(56) References Cited

U.S. PATENT DOCUMENTS 4,754,654 A * 7/1988 Johnson ................... G01N 1/14
73/864.34
5,606,138 A * 2/1997 Saarenketo ............. G01N 1/14
73/864.34

(Continued)

FOREIGN PATENT DOCUMENTS

CN        103197038 B     12/2014
CN        205396467 U  *  7/2016

(Continued)

OTHER PUBLICATIONS

International Search Report dated Jun. 4, 2019, issued in application No. PCT/CN2019/081047.

*Primary Examiner* — David A. Rogers
(74) *Attorney, Agent, or Firm* — McClure, Qualey & Rodack, LLP

(57) ABSTRACT

The present invention discloses an ocean surface water continuous sampling device, the device comprises a support that ascends and descends along the stern, on the support a sampling pipe for drawing and sampling the surface water, and hydraulic tanks for driving the support up and down to send the sampling pipe to where the surface water is are provided, and a buffer mechanism for avoiding damage due to constant water resistance to the sampling pipe during sailing is provided on the support too. Configuration of the depth transducer, control unit and hydraulic tanks, promises surface water accurate and continuous collection during research vessel travelling; the buffer mechanism works effectively in avoiding radial and axial damage to the sampling pipe due to continuous water current resistance, which successfully relieves the resistance, and prolongs (Continued)

sampling pipe life; and automatic surface water collection is realized with the automatic control design.

7 Claims, 4 Drawing Sheets

(56) References Cited

U.S. PATENT DOCUMENTS

| | | | |
|---|---|---|---|
| 6,536,272 B1 | | 3/2003 | Houston et al. |
| 6,840,121 B2 * | | 1/2005 | Thomas .................. G01N 1/14 |
| | | | 73/863.81 |
| 8,286,513 B2 * | | 10/2012 | Lange ...................... G01N 1/10 |
| | | | 73/864.63 |
| 9,545,979 B2 * | | 1/2017 | Dejean ...................... B63B 3/08 |
| 2020/0408648 A1 * | | 12/2020 | Sorensen ................. G01N 1/12 |

FOREIGN PATENT DOCUMENTS

| | | | | |
|---|---|---|---|---|
| CN | 105865841 A | * | 8/2016 | ............... G01N 1/10 |
| CN | 205785947 U | * | 12/2016 | |
| CN | 104458337 B | * | 1/2017 | |
| CN | 104677676 B | * | 2/2017 | |
| CN | 106596183 A | * | 4/2017 | ............... G01N 1/10 |
| CN | 107560897 A | * | 1/2018 | |
| CN | 108387403 A | | 8/2018 | |
| CN | 108663235 A | * | 10/2018 | ............ B63B 35/00 |
| CN | 108548696 B | * | 6/2020 | ............... G01N 1/14 |
| CN | 212363791 U | * | 1/2021 | ............... G01N 1/14 |
| CN | 214538693 U | * | 10/2021 | |
| KR | 1074586 B1 | * | 10/2011 | ............... G01N 1/14 |
| WO | WO-2019196710 A1 | * | 10/2019 | ............... G01N 1/14 |

* cited by examiner

DEVICE FOR CONTINUOUSLY SAMPLING DEEP SEA SURFACE WATER

TECHNICAL FIELD

The present invention relates to the technical field of research vessels, especially to ocean surface water continuous sampling device.

BACKGROUND TECHNOLOGY

Microplastics are a type of plastic fragment that is less than 5 mm in diameter, and are primary carriers causing pollution. Microplastics include low density polyethylene (LDPE), polypropylene, polyvinyl chloride, polystyrene, polyurethane, polyamide, and polyethylene terephthalate etc. Microplastics are of tiny volume, which means higher specific surface area (total surface area of a porous solid material per unit of mass), and the bigger is the specific surface area, the stronger is the ability to absorb pollutants. First of all, there are already a lot of persistent organic pollutants such as polychlorinated biphenyl and bisphenol A (most of these organic pollutants are lyophobic, which means that they cannot be dissolved in water, as a result, they are not floating as water does), and once microplastics meet these pollutants, they aggregate to form an organic polluting sphere. Microplastics play a role of a mount, on which the pollutants roam around.

It is pointed out in the UNEP year-book 2014 and the report Valuing plastic, that plastic pollution has affected livelihood of marine organisms and development of tourism, fishery and commerce, which improved awareness of microplastics. Generally, particle diameter of microplastics is below 5 mm, which is likely to be ingested by organisms in the "lower end" of food chain, such as zooplankton, benthonic organisms, fishes and mussels, and as it is not possible to digest such microplastics, which are swallowed, kept in stomach of animals and occupying space, causing animal illness or even death; and harm to zooplankton is even worse, when microplastics with organic pollutants are ingested, the pollutant in vivo is released under the effect of enzymes and aggravates the illness. On one hand, organism death may happen which adversely affects stability of the ecosystem, on the other hand, the harm may be extended to human when pollutants are spread to dining tables in the effect of food chains. Organisms like mussels, and zooplankton at the bottom of the food chain may be eaten by animals at higher end, the food chain is characterized by its "magnification" effect, which means, the contaminants existing in an animal at lower end may be only 1%, and upon spreading to the higher end animal, it may be magnified to 20%, which causes many illnesses or death of organisms ingesting microplastics and accompanying pollutants, as human is in the top end of food chain, there will be a lot of microplastics in human body as a result of the "magnification" effect, which are difficult to digest and may pose unpredictable threat to human health. Just like PM2.5 in the marine, microplastics threatens health of marine organisms and human. Animal experiments show that, due to tiny particle diameter, microplastics may enter tissue cell, accumulate in animal viscera, trigger infection and case damage to liver and endocrine disturbance etc.

To manage microplastics in the marine, first it is necessary to conduct an inspection on the ingredients and contents of microplastics, and evaluate how severe the pollution is and its primary source, and provide basis for consequent pollution control work. At the present, FT-IR Microscopy & Imaging Systems by Perkin Elmer and Fourier transform infrared microspectroscopy are employed in marine microplastics inspection. FT-IR Microscopy & Imaging Systems and Fourier transform infrared microspectroscopy is providing useful support for the inspection. However, to conduct the micro plastic inspection, it is necessary to sample the microplastic particles from the marine surface water and filter them first. Currently, there are two sampling methods available, static sampling and dynamic sampling at the stern or side board of a ship; it is easy to conduct a static sampling, but it is necessary to halt the ship, and not convenient to collect a large number of data to evaluate conditions over a span of sea; and for the dynamic sampling, as the ship is moving, the sea water will pose strong and lasting resistance to the sampling facilities, bringing higher demands to them. However, it is necessary and highly desirable to evaluate the microplastics pollution conditions over a span of sea by sample inspection, thus a continuous and well-proportioned sampling shall be done against it, in other words, the bigger is the sea sampling area over a span of sea, the more accurate are the sampling data, which calls for a continuous sampling. For example, in China, a variety of deep ocean sampling facilities have been independently developed, such as the one with multiple pipes, trunk type one and trawl type.

Usually, trunk type samplers are used in static sampling, as it is difficult to have the trunk fixed due to water resistance when the ship is moving, consequently, the trunk is liable to rub, crush and even damage the ship body; samplers with a trawl is not proper for stable long time sampling too, as the trawl will always twine with objects under the water, such as those in the aquacultural area or some floating matters. At present, research vessel continuous sampling is generally done during travel, by installing one or more sampling pipes on the side board, extending it/them 20-30 cm below the marine water surface, drawing sea water with the sampling pipes onboard, but there are still some shortcomings with this sampling way, first of all, as the research vessels are travelling, the sampling pipes will be subject to a constant resistance during collecting marine surface water, which may produce a floating power on the sampling pipes, rendering their position under the water unstable and it difficult to fix them on the stern; second, even if the conventional sampling pipes are well fixed on the stern, the research vessels' long and continuous travelling will always incur constant water resistance on the sampling pipes, rendering them bending and damaging; third, it is still to be solved with regard to how to firmly secure sampling pipes on the stern.

DESCRIPTION OF THE INVENTION

Targeting the deficiencies in the prior art, the present invention aims to provide a kind of adaptive dynamic sampling method and sampling device used for sampling ocean surface water continuously, by which it is not only possible to continuously collect surface water data over a large span of sea, and ensure stable sampling process, and proper sampling data and accurate water sample from designed aqueous layers, and in the meantime, it will cause no delay to the research vessels' navigation, and other marine data collection.

To address the above mentioned technical problems, the technical plan adopted by the present invention is that: an ocean surface water continuous sampling device, which includes a support which can ascend or descend along a stern; a sampling pipe for drawing and sampling surface water that is free to move both laterally and axially within a buffer housing provided on the support; a hydraulic tank for driving the support up and down, to send the sampling pipe to the surface water; a buffer mechanism, configured for avoiding damage to the sampling pipe due to water resistance during travelling provided on the support; wherein the buffer mechanism comprises a buffer housing on the support, the buffer housing comprises a buffer cavity, and on the buffer housing a mounting hole allowing the sampling pipe to pass the buffer cavity is provided; in the buffer housing, a flexible supporting assembly allowing the sampling pipe to axially and radially move freely within the mounting hole when a continuous water resistance happens is provided; at a bottom portion of the sampling pipe a depth transducer to check a distance from a sampling pipe water inlet to the water surface is provided; a control unit is provided too, wherein the depth transducer detects signals of a position of the water inlet, and sends to the control unit, which will receive the signals and deliver a signal controlling working status of the hydraulic tank, and the hydraulic tank will in turn push the support to have the sampling pipe water inlet posed at the surface water, after the sampling is done, send quit signal to the hydraulic tank, and draws the support and the sampling pipe back.

In the continuous ocean surface water sampling device, the flexible supporting assembly comprises a supporting bar passing through the submerging pipe along a water resistance direction to be fixed inside the buffer cavity, a buffer spring for undermining impact from water resistance on the sampling pipe and a supporting spring for backing the supporting bar.

The continuous ocean surface water sampling device, wherein the sampling pipe comprises a rigid submerging pipe that is free to move both laterally and axially within the buffer housing, a rigid transportation pipe in connection with the rigid submerging pipe and a flexible outlet pipe in connection with the rigid transportation pipe drawing the surface water onboard, the rigid submerging pipe and rigid transportation pipe are flange connected.

The continuous ocean surface water sampling device, wherein a connection adjustment opening is provided radially across the sampling pipe, an inner diameter of the connection adjustment opening is bigger than a diameter of the sampling pipe, and the supporting bar is located throughout the connection adjustment opening and is fixed onto inner sides of the buffer housing.

The continuous ocean surface water sampling device, wherein a bore diameter of the mounting hole is bigger than an outer diameter of the sampling pipe.

The continuous ocean surface water sampling device, wherein two hydraulic tanks are provided, symmetrically on either side of the sampling pipe and fixed on the stern.

The continuous ocean surface water sampling device, wherein the rigid submerging pipe is configured to of a trapezoid structure, with a reduced diameter top down.

Advantages of the present invention as a continuous ocean surface water sampling device: sampling device according to the present invention is installed on the stern of a research vessel, and with the configuration of depth transducer, control unit and hydraulic tanks, not only accurate surface water collection is promised, continuous sampling during travelling can be done too; with the buffer mechanism, axial and radial damage to the sampling pipe due to constant water current resistance is effectively avoided, and the resistance is to a great extent relieved, which prolongs usage life of the sampling device; at last, automatic control, enables sampling pipe depth real time adjustment depending on signals from the depth transducer, which realizes automatic surface water collection.

EMBODIMENTS

Figure 1:
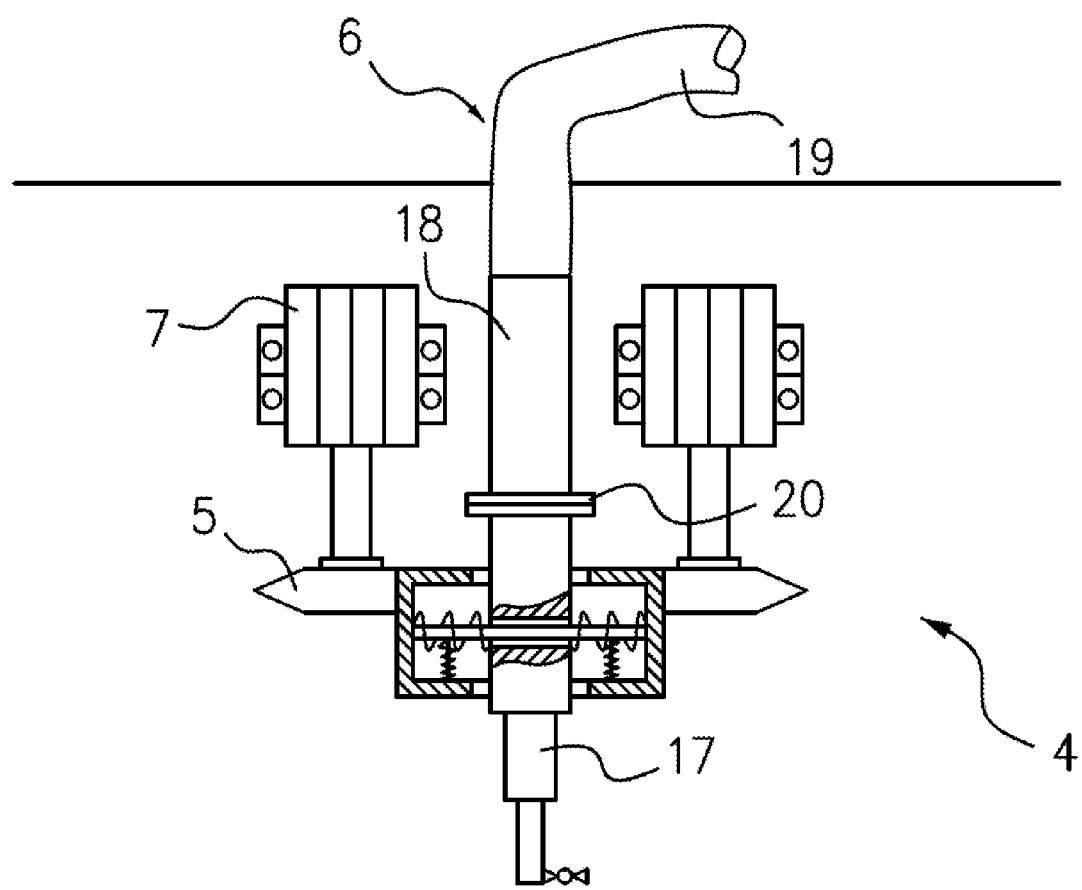
FIG. 1 is a structural view of the present invention.
Figure 2:
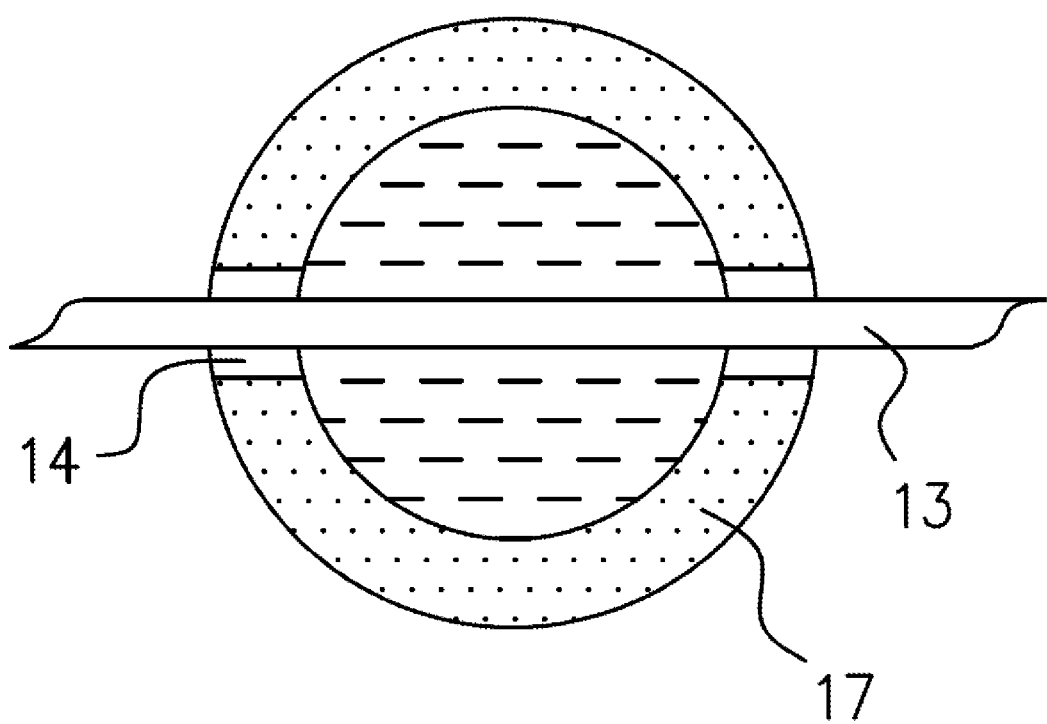
FIG. 2 is an enlarged structural view of the connection between the sampling pipe and the supporting members.
Figure 3:
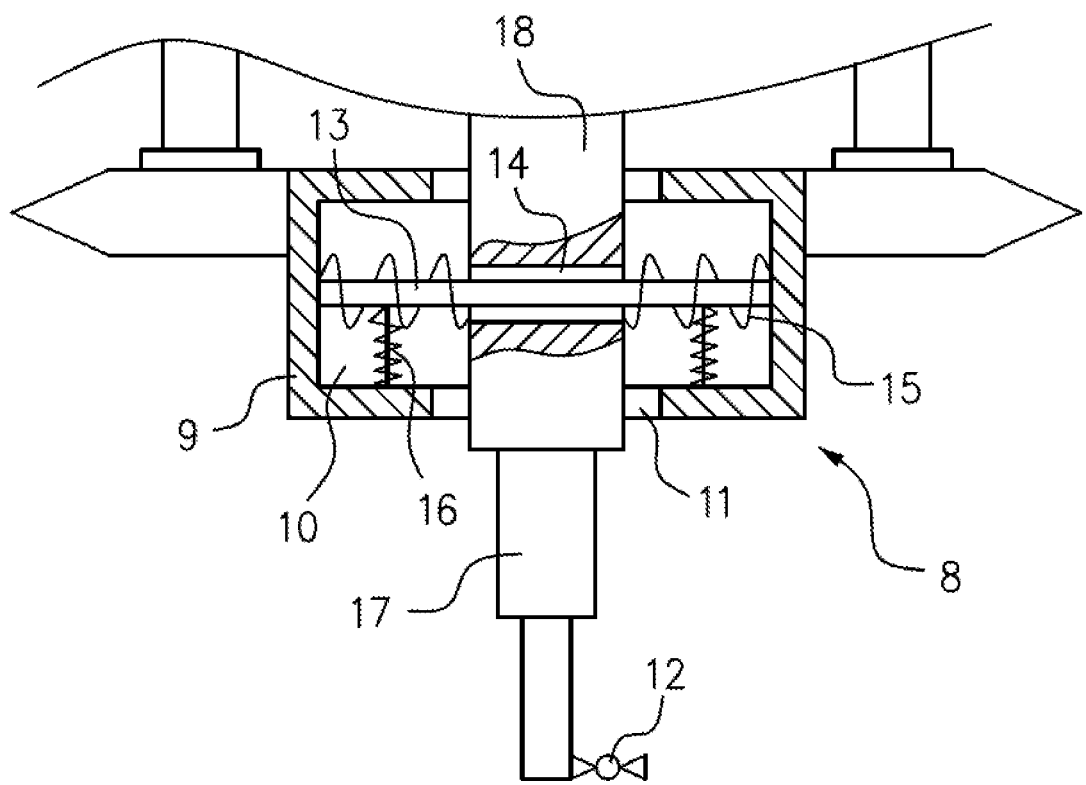
FIG. 3 is a partially enlarge view showing the buffer mechanism.
Figure 4:
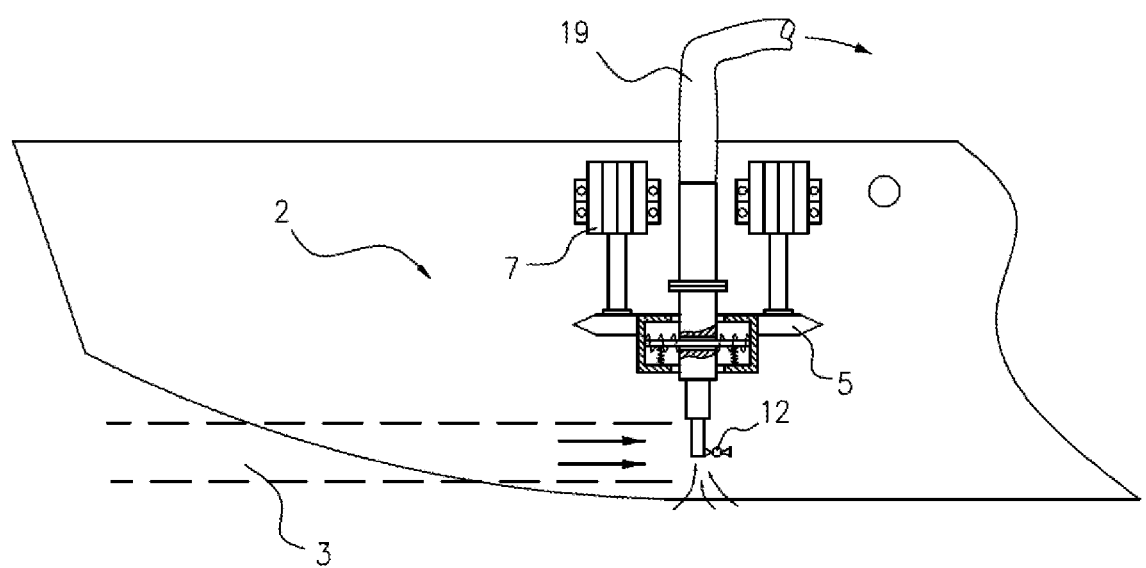
FIG. 4 is a view showing the surface water collection in the present invention.

Hereafter the present invention is more detailed explained by the accompanying drawing in conjunction with the specific embodiments:

As is shown in the FIGS. 1, 2, 3 and 4, a continuous ocean surface water sampling device 4, comprising a support 5 which may ascend or descend along the stern 2, a sampling pipe 6 for drawing and sampling surface water 3 that is free to move both laterally and axially within a buffer housing, and hydraulic tanks 7 for driving the support 5 up and down, to send the sampling pipe 6 to a position of surface water 3, and to promise support stability during ascending and descending, the hydraulic tanks 7 in the present embodiment are configured to be two, symmetrically provided on either side of the sampling pipe 6 and fixed on the stern 2. Among the prior art, the hydraulic tank 7 is a common power component, and will not be explained in details here. A buffer mechanism 8 for avoiding damage to the sampling pipe 6 due to water resistance during travelling is provided on the support 5, the buffer mechanism comprises the buffer housing 9 provided on the support 5, the buffer housing 9 comprises a buffer cavity 10, and on the buffer housing 9 a mounting hole 11 allowing the sampling pipe 6 to pass the buffer cavity 10 is provided, to avoid rigid damage to the sampling pipe 6 due to water resistance, a bore diameter of the mounting hole 11 is bigger than an outer diameter of the sampling pipe 6. In the buffer housing 9, a flexible supporting assembly allowing the sampling pipe 6 to axially and radially move freely within the mounting hole 11 when a continuous water resistance happens is provided; at a bottom portion of the sampling pipe 6 a depth transducer 12 to check a distance from a water inlet of the sampling pipe to the water surface is provided; a control unit is provided too, wherein the depth transducer 12 detects signals of a position of the water inlet, and sends to the control unit, which will receive the position signals and deliver a signal controlling working status of the hydraulic tanks 7, which will push the support 5 to pose the water inlet of the sampling pipe at the surface water, after sampling is done, send quit signal to the hydraulic tank 7, and draws the support 5 and the sampling pipe 6 back. Generally, ocean surface water 3 covers water 20-30 centimeters under the water surface.

The said continuous ocean surface water sampling device, wherein the flexible supporting assembly comprises a supporting bar 13 provided across the sampling pipe 6 along a water resistance direction to be fixed inside the buffer cavity 10, a connection adjustment opening 14 is provided radially across the sampling pipe 6, and to avoid effects of the water resistance on the sampling pipe 6 and leave rigid damage, an inner diameter of the connection adjustment opening 14 is bigger than a diameter of the sampling pipe 6, and a supporting bar 13 is located throughout the connection adjustment opening 14 and is fixed onto inner sides of the buffer housing 9. A buffer spring 15 for undermining impact from the water resistance on the sampling pipe 6 and supporting springs 16 for backing the supporting bar are provided on the supporting bar 13. In the present invention, the sampling pipe 6 comprises a rigid submerging pipe 17 fixed on the buffer housing 9, a rigid transportation pipe 18 in connection with the rigid submerging pipe 17 and a flexible outlet pipe 19 in connection with the rigid transportation pipe 18 drawing the surface water onboard, the rigid submerging pipe 17 and the rigid transportation pipe 18 are connected by a flange 20. Since a sampling pipe 6 of a bigger size will be subject to larger influence from the water resistance, the said rigid submerging pipe 17 is configured to be of a trapezoid structure, wider on top and shorter down.

Generally, during travelling, resistance that a sampling pipe 6 is bearing comes primarily from seawater in the navigation direction and transverse water current against the sampling pipe 6, however, resistance due to the transverse water current is usually small, which will not substantially impact the sampling pipe 8, with the buffer mechanism 8, it is not only possible to reduce primary resistance from seawater in the navigation direction, but will also relieve the transverse resistance, which will always promise stability of the sampling pipe 6.

Apparently, the above explanation is not a limitation on the present invention, and the present invention shall not be limited to the above embodiments, variations, modifications, addition and replacement made by those of common skill in the art, within the substantial scope of the present invention falls within the protection of the present invention.

What is claimed is:

1. An ocean surface water continuous sampling device, characterized in that: the device comprises
   a support which ascends or descends along a stern;
   a sampling pipe for drawing and sampling surface water that is free to move both laterally and axially within a buffer housing provided on the support;
   a hydraulic tank for driving the support up and down, to send the sampling pipe to the surface water; and
   a buffer mechanism, configured for avoiding damage to the sampling pipe due to water resistance during travelling provided on the support;
   wherein the buffer mechanism comprises the buffer housing provided on the support, the buffer housing comprises a buffer cavity, and on the buffer housing a mounting hole allowing the sampling pipe to pass the buffer cavity is provided; in the buffer housing, a flexible supporting assembly allowing the sampling pipe to axially and radially move freely within the mounting hole when a continuous water resistance happens is provided; at a bottom portion of the sampling pipe a depth transducer to check a distance from a sampling pipe water inlet to the water surface is provided; a control unit is provided too, wherein the depth transducer detects signals of a position of the sampling pipe water inlet, and sends to the control unit, which will receive the signals and deliver a signal controlling working status of the hydraulic tank, and the hydraulic tank will in turn push the support to have the sampling pipe water inlet at the surface water, after sampling is done, send a quit signal to the hydraulic tank, and draws the support and the sampling pipe back.

2. The ocean surface water continuous sampling device according to claim 1, wherein the flexible supporting assembly comprises
   a supporting bar passing through the submerging pipe along a water resistance direction to be fixed inside the buffer cavity,
   a buffer spring for undermining impact from the water resistance on the sampling pipe, and
   a supporting spring for backing the supporting bar.

3. The ocean surface water continuous sampling device according to claim 1, wherein the sampling pipe comprises
   a rigid submerging pipe that is free to move both laterally and axially within the buffer housing,
   a rigid transportation pipe in connection with the rigid submerging pipe, and
   a flexible outlet pipe in connection with the rigid transportation pipe drawing the surface water onboard,
   wherein the rigid submerging pipe and rigid transportation pipe are flange connected.

4. The ocean surface water continuous sampling device according to claim 2, wherein a connection adjustment opening is provided radially across the sampling pipe, an inner diameter of the connection adjustment opening is bigger than a diameter of the sampling pipe, and the supporting bar is located throughout the connection adjustment opening and is fixed onto inner sides of the buffer housing.

5. The ocean surface water continuous sampling device according to claim 1, wherein a bore diameter of the mounting hole is bigger than an outer diameter of the sampling pipe.

6. The ocean surface water continuous sampling device according to claim 1, wherein two hydraulic tanks are provided, symmetrically on either side of the sampling pipe and fixed on the stern.

7. The ocean surface water continuous sampling device according to claim 3, wherein the rigid submerging pipe is configured to be of a trapezoid structure, with a reduced diameter top down.

\* \* \* \* \*